United States Patent
Casanova et al.

(10) Patent No.: US 11,376,443 B2
(45) Date of Patent: Jul. 5, 2022

(54) PASSIVE RESONATOR AND METHOD OF USE FOR BRAIN WAVE ENTRAINMENT

(71) Applicant: University of South Carolina, Columbia, SC (US)

(72) Inventors: Manuel F. Casanova, Simpsonville, SC (US); Estate M. Sokhadze, Greenville, SC (US)

(73) Assignee: University of South Carolina, Columbia, SC (US)

( * ) Notice: Subject to any disclaimer, the term of this patent is extended or adjusted under 35 U.S.C. 154(b) by 443 days.

(21) Appl. No.: 15/915,388

(22) Filed: Mar. 8, 2018

(65) Prior Publication Data
US 2018/0256913 A1 Sep. 13, 2018

Related U.S. Application Data

(60) Provisional application No. 62/468,410, filed on Mar. 8, 2017.

(51) Int. Cl.
*A61N 5/02* (2006.01)
*A61N 1/40* (2006.01)
*A61N 5/04* (2006.01)
*A61N 2/00* (2006.01)
*H01Q 1/27* (2006.01)

(52) U.S. Cl.
CPC ............... *A61N 5/022* (2013.01); *A61N 1/40* (2013.01); *A61N 2/006* (2013.01); *A61N 5/04* (2013.01); *H01Q 1/276* (2013.01)

(58) Field of Classification Search
CPC . A61N 1/40; A61N 5/04; A61N 5/022; A61N 2/006; H01Q 1/276
See application file for complete search history.

(56) References Cited

U.S. PATENT DOCUMENTS

| | | | |
|---|---|---|---|
| 9,320,913 B2 * | 4/2016 | Dimino | A61N 2/02 |
| 2003/0028072 A1 * | 2/2003 | Fischell | A61N 1/32 |
| | | | 600/13 |
| 2006/0149337 A1 * | 7/2006 | John | A61N 1/36082 |
| | | | 607/45 |

OTHER PUBLICATIONS

Beck RC. Preliminary research report ELF magnetic fields and EEG entrainment, 1978 http://www.elfis.net/elfol8/e8elfeeg2.htm.
Bell G, Marino AA, Chesson AL. Alterations in brain electrical activity caused by magnetic fields: detecting the detection process. Electroenphalography and Clinical neurophysiology 83:389-397, 1992.
König HL, Unsichtbare Umwelt, Eigenverlag Herbert L. König, München, 1977.

(Continued)

*Primary Examiner* — Mallika D Fairchild
(74) *Attorney, Agent, or Firm* — Dority & Manning, P.A.

(57) ABSTRACT

A system and method designed to encourage entrainment of brain waves with a therapeutic wave of a predetermined frequency. The system uses antennae to emit a modulated high frequency carrier signal that carries the therapeutic signal. The system can be utilized in modification of brain-wave frequencies in a local or global scale and/or in establishing coherence between different cortical regions. The system can be utilized in treatment of individuals suffering from mental disorders and can be utilized to enhance/improve function in otherwise mentally healthy individuals.

12 Claims, 1 Drawing Sheet

(56) References Cited

OTHER PUBLICATIONS

Kramarenko AV, Tan U. Effects of high-frequency electromagnetic fields on human EEG: a brain mapping study. Int J Neurosci 113(7): 1007-19, 2003.

Persinger MA, Richards PM, Koren S. Differential entrainment of electroencephalographic activity by weak complex electromagnetic fields. Perceptual and Motor Skills 84:527-536, 1997.

Pugh O. What is the amperage of the electric current running through neurons? MadSci Network: Cell Biology http://www.madsci.org/posts/archives/2000-04/955661195.Cb.r.html.

Raz A. Could certain frequencies of electromagnetic waves or radiation interfere with brain function? Scientific American Apr. 24, 2006. http://www.scientificamerican.com/article/could-certain-frequencies/.

Rensberger B, Jell-O test finds lifelike signal, NY Times Mar. 6, 1976: C6.

Schlegel K, Füllekrug M, 50 Years of Schumann Resonance. Physik in unserer Zeit, 33(6),: 256-26, 2002. A version translated into English can be found at: http://www.hese-project.org/hese-uk/en/niemr/50_vrs_schumann.pdf.

Abstract of Von Klitzing L. A new ecephalomagnetic effect in human brain generated by static magnetic fields. Brain Research 540:295-296, 1991.

Wheeler M, Hyperactivity in brain may explain multiple symptoms of depression. UCLA Newsroom, Feb. 27, 2012. http://newsroom.ucla.edu/releases/hyperactivity-in-brain-may-explain-228954.

Dogris N. Neurofield. Neuroconnections. International Society for Neurofeedback and Research, pp. 21-24, 2009.

Evans Jr. Historical overview of rhythmic stimulation procedures in health and disease. In JR Evans and RP Turner (eds.) Rhythmic Stimulation Procedures in Neuromodulation. American Academy Press, London, UK, ch. 1, pp. 1-31, 2017.

Meyers BA. PEMF: The 5th element of health. Balboa Press, Bloomington, Indiana, 2014.

Wilfried A, Nowak H. Magnetism in Medicine: A Handbook. Wiley, New York, 2007.

\* cited by examiner

PASSIVE RESONATOR AND METHOD OF USE FOR BRAIN WAVE ENTRAINMENT

CROSS REFERENCE TO RELATED APPLICATION

This application claims filing benefit of U.S. Provisional Patent Application Ser. No. 62/468,410 having a filing date of Mar. 8, 2017, which is incorporated herein by reference for all purposes.

BACKGROUND

The brain provides for centralized control over our bodily and mental activities through the coordinated action of neurons. To function effectively, neurons in different regions of the brain should operate in coherence with one another so as to properly process input as is necessary for comprehension of the environment and for carrying out tasks. For instance, it is well established that regular periods of deep sleep, when brain neurons are operating in coordination at low frequencies (about 1 Hz to about 4 Hz delta waves), is necessary for healthy existence. Likewise, periods of intense concentration require multiple regions of the brain to operate in coordination with one another at higher frequencies (e.g., about 30 Hz to about 100 Hz). A lack of coherence in neuron function between different areas of the brain can lead to a mental disorder and, in extreme situations, even death.

Approximately one in four individuals in the general population meet diagnostic criteria for a mental disorder. Gold standards for psychiatric diagnosis and treatment require multiple visits, psychological screening examinations and extended treatments over many years, if not a lifetime. Current therapeutic attempts rely primarily on pharmacological interventions that are aimed at containing symptoms rather than providing a cure for a specific condition and addressing the underlying biological problem of incoherent signaling between regions of the brain. Moreover, many pharmacological therapies often have serious side effects.

Attempts have been made to improve neuronal function and coordination by using various electromagnetic mechanisms. One common mechanism is the induction of electricity by the action of a varying magnetic field upon anatomical elements within the brain. This is the basic mechanism of action by which Transcranial Magnetic Stimulation (TMS) works. TMS has been approved by the FDA as a therapeutic modality for treatment-resistant depression. A second approach for treatment has been passing an electric current through the brain in electroconvulsive therapy (ECT or shock treatment) in which the applied current triggers a brief seizure. ECT is currently used in major depression, mania and catatonia. Other treatment approaches include neurofeedback in which a person is trained by watching a real-time display of brain activity. Neurofeedback is commonly used in attention deficit hyperactivity disorder (ADHD).

Neural or brainwave entrainment is another known treatment approach that causes the brain to synchronize its frequency with a periodic sensory stimulus like sound, vibration or light. Probably the earliest use of acoustic neural entrainment was the beating of drums at a constant rate in shamanic rituals. Entrainment using electromagnetic fields has been achieved using solenoids to produce small magnetic fields at the nano- and/or micro-Tesla range (Persinger et al., 1997). This technique has been used within several experimental contexts (von Klitzing, 1991; Bell et al., 1992) and can be considered a merger between brainwave entrainment and TMS. Light and sound machines that entrain brainwaves are well known and commercially available. Apparatuses and methods using square waves or sound to control photic stimulation have also been described, e.g., see U.S. Pat. No. 8,579,793 B1 and U.S. Patent Application Publication No. 2013/0131537.

One major problem with many of the aforementioned electrophysiological interventions is that they work or are administered at a different energy level from that observed in the normal brain. In a typical synapse, the response may be only a few picoAmps ($10^{-12}$ Amps) for a fraction of a second. In contrast, ECT passes approximately 900 mA through the brain and the current is sustained for several seconds. Electrophysiological methods in this regard bombard the brain with stimuli of much higher amplitudes to what it is accustomed. The end result in using such electromagnetic-based therapies for the brain is the induction of a signal whose effects may be non-linear and non-physiological.

What is needed are devices and methods that can improve brain function while working within the physiological limits of this organ.

SUMMARY

According to one embodiment, disclosed is a method for entrainment of brain waves, for instance so as to encourage the brain to exhibit coherent function among selected brain regions. A method can include generating a carrier wave in the megahertz (MHz) or gigahertz (GHz) range (e.g., about 0.5 MHz or greater) and modulating the carrier wave by use of an "entrainment wave" that contains the intelligent signal. The entrainment wave can be at a target brain wave frequency. For instance, the entrainment wave can be at a frequency of from about 1 Hz to about 100 Hz. A method can also include emitting the modulated carrier wave from an antenna that is located near or apposed to the head of a subject (e.g., about 10 cm or less from the subject's head) such that the emitted modulated carrier wave is directed to the subject's brain. Single or multiple antennae or leads radiating the modulated wave can encourage sympathetic resonance with the brain's neurons. This sympathetic resonance can establish or improve coherence between different areas of the subject's brain and improve overall brain function.

The method can be beneficially utilized in treatment applications as well as in high functioning applications such as in the treatment of mental disorders and/or improvement in concentration and other cognitive abilities.

Also disclosed is a system for entrainment of brain waves that can include a function generator configured for generating the modulated carrier wave and an antenna in electrical communication with the function generator configured to emit the modulated carrier wave and direct the wave to a subject's brain. A system can include additional antennas, voltage amplifiers, etc., and can include capabilities for focusing and/or targeting the modulated carrier wave(s) to particular areas of the brain.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Figure 1:
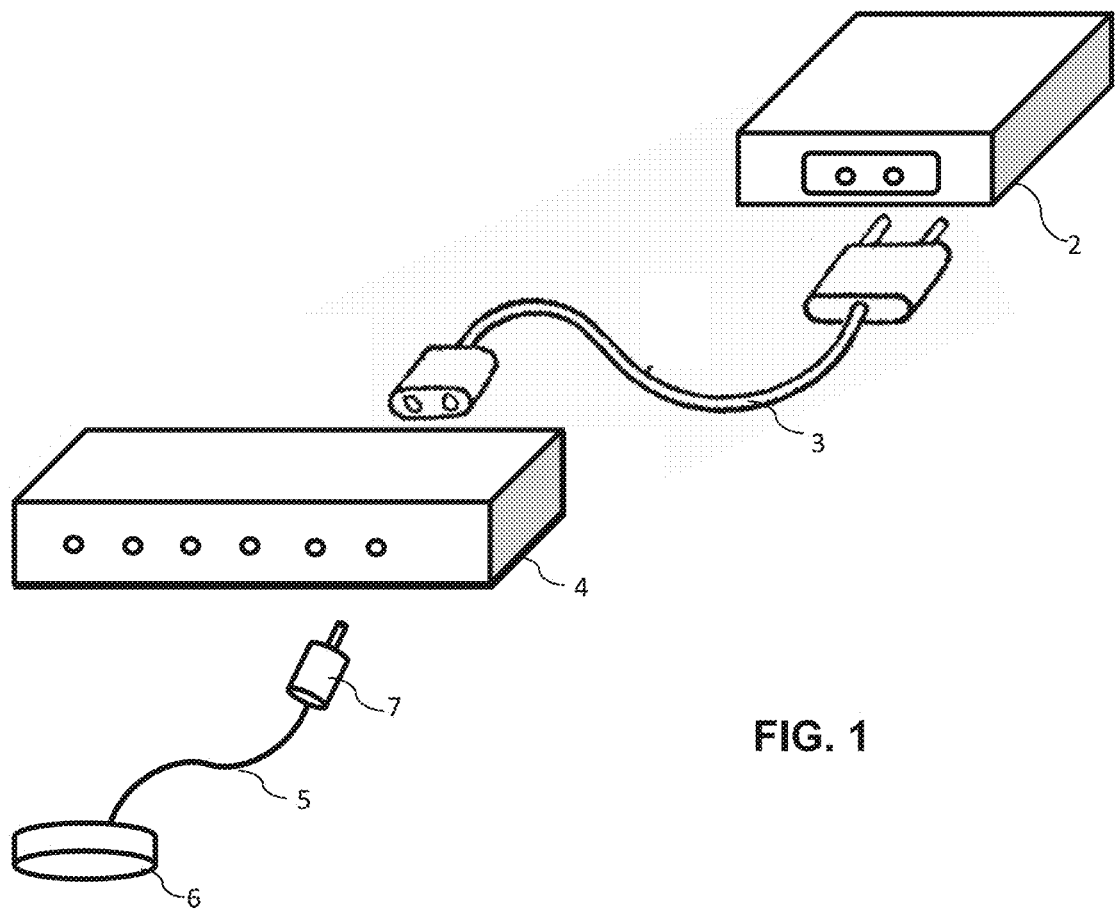
FIG. 1 illustrates several components of a system as described herein and illustrating a single antenna.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, the present disclosure is directed to a system designed to encourage entrainment of brain waves with a therapeutic or "intelligent" wave of a predetermined frequency emitted by the system and carried to the brain by use of a higher frequency carrier signal. Thus, the system can function as a sympathetic resonator and can be utilized in modification of brainwave frequencies on a global scale and/or in establishing coherence between different cortical regions. Rather than forcing neurons to fire action potentials, as is common in currently used high stimulation devices, disclosed systems can increase the probability of neurons firing in a more coherent, unified fashion.

The device can be designed to function over a wide range of applications and as such can allow personalized treatments to individuals with a variety of mental disorders. Use of the systems is not limited to treatment of individuals suffering from mental disorders however, and in other embodiments, the systems can be utilized to enhance/improve function in otherwise mentally healthy individuals, for instance to increase attention skills and cognitive performance, to encourage relaxation, improve sleep patterns, etc.

In one embodiment, the system can function at low voltage and low power and can cause little or no side effects. Through targeting a source of mental disturbance, e.g., incoherence of neuron firing within and across brain regions, use of the system can address core pathological features of mental disorders and reduce or remove the need for pharmacological interventions. As such, therapeutic approaches that incorporate use of the system can reduce time and cost of treatment and decrease expenditure involved with traditional medical interventions (e.g., drugs, hospitalization).

Referring to FIG. 1, one embodiment of a system is illustrated. As shown, the system can generally include a power supply 2, a function generator 4, and at least one antenna 6. The system is designed to deliver the entrainment signal to the brain by use of a signal that in one embodiment can be generated at a relatively low voltage (e.g., about 50 V or less) and low power (e.g., about 100 mW per $cm^2$ or less). For instance, the power supply can provide power at a voltage of from about 3 V to about 10 V, or from about 5 V to about 6 V in some embodiments. As such, in some embodiments the power supply 2 can be a relatively low voltage power supply that may be a battery, linear or switch-mode power supply, capacitor or the like. A low power design can allow for potential harmful thermal effects to be avoided, size and bulk of the system to be quite small, and high-frequency emitting antennas to be used for delivery of the entrainment signal to a subject. However, it should be understood that a lower power design is not a requirement of the system and in other embodiments a higher power signal may be preferred. Accordingly, in some embodiments a system can include a voltage amplifier to increase radiation from the antenna.

The antenna 6 can be a high-frequency emitting antenna that can operate while being located relatively close to the subject (e.g., about 10 cm or less from a subject's head), and does not give rise to dangers such as sparking, which could convert the apparatus into an electrical lancet, as may occur with present day high-energy apparatus.

The power supply 2 is in electrical communication with a function generator 4, for instance by use of a removable cable 3. It should be understood that while Illustrated as a single unit in the illustrated embodiment, the function generator 4 can be provided in any suitable fashion, with all electronics contained within a single housing, as illustrated, or alternatively is separate housings, as is known.

The function generator 4 (alternatively referred to as a signal generator) includes electrical components as are known in the art for the formation of a carrier wave of desired frequency, voltage amplitude and wave shape (e.g., sinusoidal, square, triangle, sawtooth, etc.), capacity for amplification of the voltage, as well as a modulation circuit configured for modulation of the carrier wave with an entrainment signal as described. By way of example, the function generator 4 can include one or more oscillator assemblies as are generally known in the art that can govern the frequency of the electrical signals produced and that can be formed of conventional elements.

In one embodiment, the function generator 4 can include a microcontroller that can include a timing element that can be either a mechanical resonant device, such as a crystal or a ceramic resonator, or that can be based on electrical phase-shift circuits such as an RC oscillator. In one embodiment, the microcontroller and/or oscillator assemblies used to generate the electrical signals of the system can be specifically designed to interact with living, organic systems.

The function generator 4 can include one or more integrated circuits that can shape the signals as desired. The function generator 4 can include additional components as well such as a reflectometer (that can provide a measure of impedance matching and reflected waves) or an antenna tuner (to better match the impedance of the function generator to the antenna's feedline).

Even at the highest frequencies, brain wave frequencies are lower than 100 Hz, with correspondingly long wavelengths, i.e., more than 10,000 kilometers. Because of the difficulty in building antennas that can emit such low frequencies, the disclosed system uses a high frequency carrier wave to carry the desired information or intelligence (i.e., the desired entrainment brain wave frequency) to the brain. Accordingly, the function generator 4 can produce as output a single signal that includes both the carrier wave and the information-carrying entrainment wave.

In accord with this approach, the function generator 4 can generate the high frequency carrier wave and can include a modulation circuit that can modulate the carrier wave with an entrainment wave. The modulated carrier wave thus produced from the function generator 4 can then be delivered to one or more antennas 6 for emission/radiation directed to the brain. Thus, the carrier wave is used to carry the desired entrainment information to a subject's brain. In order to prevent undesirable side effects, the carrier wave can be at a frequency that is well above the response capabilities of the brain or the human ear. For practical purposes this carrier frequency as well as its sidebands (for those embodiments in which the carrier wave is modulated via amplitude modulation) can be invisible to the brain. For instance, the carrier wave can have a frequency in the KHz, MHz or GHz range. By way of example, the carrier wave can have a frequency of from about 500 kHz to about 300 GHz, from about 1 MHz to about 100 GHz, or from about 10 MHz to about 1 GHz in some embodiments.

Riding on this carrier wave as a modulating signal can be the desired low frequency entrainment or intelligent signal that can be used to affect the subject's brain. The entrainment wave can have a frequency that can be selected for the particular behavioral demand. In general, the entrainment wave can have a frequency equivalent to the desired brain wave for mediating a particular behavioral state, i.e., between about 1 Hz and about 100 Hz. However, in some embodiments higher harmonics of a natural brain wave frequency may be incorporated as a modulating signal or as a component of a modulating signal.

The entrainment wave frequency can be selected such that the system can function as a sympathetic resonator capable of establishing resonance between the entrainment wave and brain elements in targeted regions of the brain. As such, the system can modify the subject's brain waves and thereby adjust the subject's brain wave frequencies according to the desired behavioral state for that individual. In effect, the system can function as a non-invasive pacemaker for the brain in which the low frequency component of the modulated wave produced by the function generator 4 can be radiated to the brain to interact with the subject's brain waves.

In one embodiment, the function generator 4 can be a high-end function generator as is known in the art having the inbuilt capacity to produce the desired modulated waveform of the modulated carrier wave. A typical function generator 4 can be capable of producing any of a variety of carrier waveforms at high frequencies (e.g., MHz or GHz) as well as allowing for the adjustment of the voltage level and the selection of any of a variety of analog and/or pulsed modulation techniques as may be utilized in modulating the carrier wave with the entrainment wave. For instance, the modulated carrier wave can be pulsed with pulses generated on the order of microseconds that can be constant or varied, as desired. Moreover, the function generator 4 can provide for variability with regard to the depth of modulation and the source for coupling between the carrier wave and the entrainment wave (i.e., internal or external to the function generator).

It should be understood that the disclosed systems are not limited to utilization of a high-end function generator and there are multiple circuits known in the art as may be utilized that are capable of modulating a carrier wave signal. For instance, there are relatively simple circuits known in the art that can allow miniaturization of such a system. These circuits can use crystals, audio transformers, transistors, or audio operational amplifiers (e.g., the LM358 dual operational amplifier available from Texas Instruments). The radiated waveforms of such simple circuits are generally of very low power, and they may be of use in applications such as the treatment of insomnia or increasing the attention skills of gamers as may be used in a non-clinical portable system designed for use in the home.

In one particular embodiment, the carrier wave modulation can be carried out according to an amplitude modulation methodology, in which the amplitude of the carrier signal is varied in accordance with the instantaneous amplitude of the modulating signal (i.e., the entrainment wave). Amplitude modulation can be carried out according to any standard approach including, without limitation, double-sideband modulation (e.g., double-sideband modulation with carrier, double-sideband suppressed-carrier transmission, double-sideband reduced carrier transmission), single-sideband modulation (e.g., single-sideband modulation with carrier, single-sideband modulation suppressed carrier modulation), vestigial sideband modulation, or quadrature amplitude modulation. However, it should be understood that carrier wave modulation techniques are not limited to amplitude modulation, and any other analog or pulse modulation technique as is known in the art is likewise encompassed herein. For example, the carrier wave can be modulated via an angular modulation approach including, without limitation, frequency modulation, phase modulation, or transpositional modulation.

In general, the function generator 4 can include a modulation circuit that is connected to the power supply 2 and to a ground potential. A first input to the modulation circuit connects the carrier signal (e.g., generated by a first oscillator assembly or microcontroller) to the modulation circuit and a second input to the modulation circuit connects to the modulating signal (e.g., the entrainment wave generated by a second oscillator assembly or second microcontroller) to the modulation circuit. The resultant modulated wave form produced as output from the modulation circuit includes the entrainment wave at the desired frequency intended to cause brainwave resonance.

The modulated signal generated at the function generator 4 can then be passed to the antenna 6, for instance via an LC circuit. Though illustrated with a single antenna in FIG. 1, the entrainment-based system can generally include multiple antennae that can each direct the modulated signal carrying the entrainment wave to a particular brain region and establish sympathetic resonance with the targeted region without necessarily controlling the resultant brainwave frequency. As such, the system can enable entrainment at specific pre-determined frequencies and at specific targeted brain sites. The use of multiple antennae can thus help establish coherence between different brain regions As utilized herein, the term "antenna" is intended to refer to a device that is not intended to set up a flow of current between the apparatus and the patient, as is the case with electrodes, but rather refers to a device that need not have any direct electrical contact with the subject and operates in contact or non-contact mode with the subject. In general, an antenna is fed by only one conductor, and any antennae as are known in the art including loop antennae are encompassed herein. The particular shape and size of the emitting antenna can be varied, as can communications method between the antenna 6 and the function generator 4, as is known. Variations in antenna characteristics can be utilized to modify the emissions, for instance with regard to direction and power density delivery at a targeted location within the brain of a subject.

Figure 2:
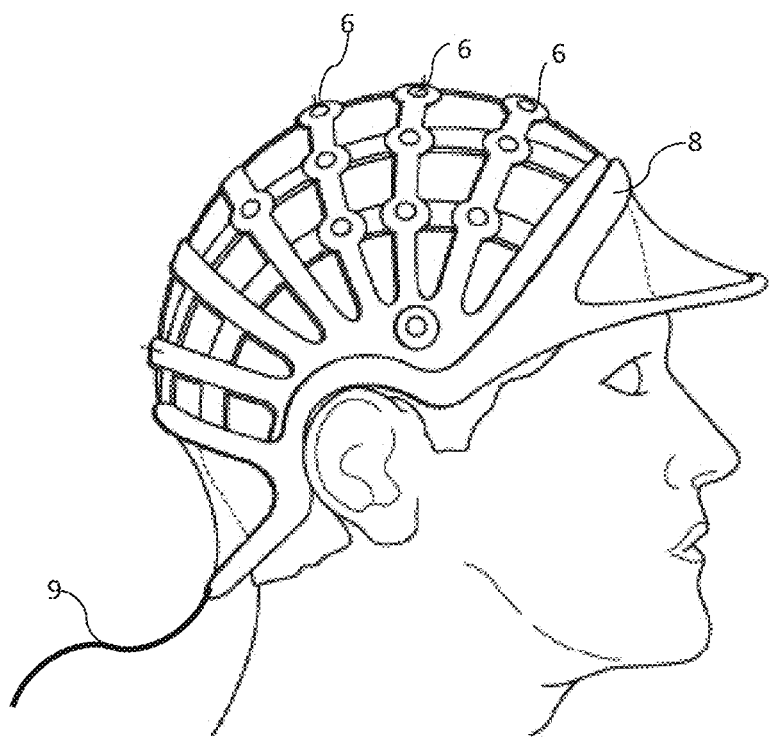
FIG. 2 illustrates components of a system as described herein including a helmet configured for carrying a plurality of antennae.

In one embodiment, the antenna 6 can be a flexible antenna as may be easily attached to a subject's head or a carrier structure (e.g., a helmet as illustrated in FIG. 2). For instance, an antenna 6 can include a flexible support on which the antenna is printed in a conductive circuit for emitting the modulated signal generated at the function generator 4. Similarly, the antenna can include a wire bonded to a support, e.g., a flexible support. In one embodiment, an antenna can be retained within a housing, e.g., within a helmet or protective covering. A housing or covering can prevent surface phenomena that can arise from direct contact between the conductive emission circuit and the subject's skin.

During use, the antenna 6 can be applied directly to a subject's head as the electromagnetic field produced thereby can be at low power and thus present little or no possibility of negative thermal or electrical effects on the subject's body. In general, the conductive circuit of an antenna 6 can be separated from a subject, even in those embodiments in which an antenna is directly attached to the subject. For instance, the conductive circuit can be insulated from a subject by use of, for example, a simple lacquer with which the circuit can be coated or an insulating material sheath or pouch. The pattern of conductive material that forms the antenna can be varied according to known methodology to allow for the distribution of the electric field emitted from the antenna 6 to be accurately determined and in a predetermined energy density.

By way of example and without limitation, an antenna can include a conductive material printed or otherwise formed in pattern including two spirals joined at both ends, with one end being connected to the function generator 4 by means of a conductive wire 5 and a suitable adapter 7. In one particular embodiment, a function generator 4 can be connected to an antenna 6 by using an N-type male plug to a BNC female jack straight coaxial RF connector that can be applied at the output of the function generator 4. A male and female CCTV 2-wire BNC adapter can then be used to serially connect the coaxial cable to a potentiometer (set to 50 Ohm for impedance matching) and then to the antenna. These connections can be made through the positive ends of the coaxial cable. Negative ends of the CCTV 2-wire BNC adapters can be grounded The use of a removable attachment, e.g., adapter 7, to the function generator 4 can allow for the antenna to be interchangeable with another antenna designed for emission of another signal, e.g., a different carrier wave, entrainment wave, or both. It may also be useful to utilize an interchangeable antenna in those embodiments in which a system is designed for use with multiple subjects. For instance, a single signal generator can be utilized with multiple subjects by merely changing out the antenna, thereby preventing indirect contact and contamination between subjects.

The antenna 6 can serve to optimize and control the emitted radiation (e.g., the strength of the radiated field in a given direction) so as to maximize coupling of the energy from the function generator 4 to free space. Beneficially, the antenna 6 can be configured to be located at a distance from the subject that can be very small (e.g., about 10 cm or less from a subject's head), which can provide for little attenuation of the modulated signal. As such, the entrainment wave carried by the modulated signal can function in near field (i.e., less than one wavelength from the antenna), Function in near field can be beneficial as in the near field the nature of the wave depends on source characteristics rather than on the propagation medium. Also, in near field the use of high currents/low voltages provide for mainly magnetic radiation or effects.

While a system can utilize a single antenna, in some embodiments, a system can include a plurality of antennae. One embodiment of which is illustrated in FIG. 2 in which the plurality of antennas 6 are retained on a helmet 8 that can be in electrical communication via cable 9 with a signal generator as discussed previously. The use of multiple antennas can help entrain multiple brain areas with a single resonant signal so as to develop coherence in medical conditions where neural binding has been shown to be abnormal (e.g., autism, schizophrenia). Inclusion of a helmet 8 or other carrier system for a plurality of antenna 6 can also be useful for non-clinical applications, such as sleep or concentration enhancement, in which targeting and control specifications of the modulated carrier wave emitted by the antenna is not as critical.

Disclosed systems can be used to establish sympathetic resonance in multiple medical conditions including, without limitation, autism spectrum disorder and those previously diagnosed as Asperger syndrome, dyslexia and other learning disabilities, ADHD, major depression, schizophrenia, treatment and rehabilitation of stroke victims, Alzheimer's disease, mild cognitive impairment, face blindness, bipolar disorder, Parkinson's disease, dystonia, essential tremor, traumatic brain injury or head injury, anxiety disorders, sleep disturbances (dyssomnias, parasomnias, circadian rhythm disorders, and sleeping sleekness), pain (including causalgia), epilepsy/seizures, addiction, and dependence, electromagnetic hypersensitivity, eating disorders, automatic behavior (narcolepsy), high blood pressure, headaches, tinnitus, chronic fatigue, obsessive compulsive disorders (OCD), and Post-traumatic stress disorder (PTSD).

When considering non-clinical applications, disclosed systems can be useful in sleep improvement (e.g., ability to fall and remain asleep in cases of insomnia), as well as aiding individuals to remain alert (e.g., in the case of fighter pilots, traffic controllers, long distance drivers, and gamers). The device may also be of help as a way of enhancing cognitive skills as for example: during ageing, to promote energetic focus in athletes or to induce a sedated or relaxed state.

In one embodiment, utilization of the system can be combined with neurofeedback and/or cognitive behavioral therapy (CBT) or other traditional therapies, including pharmacological therapies, for improved outcomes.

While certain embodiments of the disclosed subject matter have been described using specific terms, such description is for illustrative purposes only, and it is to be understood that changes and variations may be made without departing from the spirit or scope of the subject matter.

What is claimed is:

1. A method for entrainment of brain waves comprising:
   generating a carrier wave;
   modulating the carrier wave by an entrainment wave;
   emitting a resulting modulated carrier wave from a first antenna located 10 cm or less from a surface of a subject's head and directing the emitted modulated carrier wave from the first antenna to a first cortical region of the subject's brain;
   emitting an identical modulated carrier wave from a second antenna located 10 cm or less from the surface of the subject's head and directing the identical emitted modulated carrier wave from the second antenna to a second, different cortical region of the subject's brain; wherein
   the modulated carrier waves encourage sympathetic resonance between neurons of the first cortical region, neurons of the second cortical region, and the entrainment waves of the modulated carrier waves, and thereby establish coherence in neuronal firing frequency between the first cortical region and the second cortical region of the subject's brain.

2. The method of claim 1, wherein the carrier wave has a frequency of 500 kHz or higher.

3. The method of claim 1, wherein the entrainment wave has a frequency of from 1 Hz to 100 Hz.

4. The method of claim 1, comprising emitting the modulated carrier wave from additional antennae, all of which being located within 10 cm of the surface of the subject's head.

5. The method of claim 1, wherein the method increases the probability of the neurons of the first and second cortical regions of the subject's brain firing at the frequency of the entrainment wave.

6. The method of claim 1, wherein the carrier wave is modulated by the entrainment wave according to an amplitude modulation methodology.

7. The method of claim 1, wherein the carrier wave is modulated by the entrainment wave according to an analog or pulse modulation methodology.

8. The method of claim 1, wherein the antenna is attached to the subject's head.

9. The method of claim 1, wherein the antenna is retained on a carrier.

10. The method of claim 9, wherein the carrier comprises a helmet.

11. The method of claim 1, wherein the method is carried out in treatment of a medical condition or a mental disorder.

12. The method of claim 1, wherein the method is carried out in a non-clinical application.

* * * * *